US010403753B2

(12) United States Patent
Jonker et al.

(10) Patent No.: US 10,403,753 B2
(45) Date of Patent: Sep. 3, 2019

(54) CONTROLLING STRUCTURAL PHASE TRANSITIONS AND PROPERTIES OF TWO-DIMENSIONAL MATERIALS BY INTEGRATING WITH MULTIFERROIC LAYERS

(71) Applicant: The Government of the United States of America, as represented by the Secretary of the Navy, Arlington, VA (US)

(72) Inventors: Berend T. Jonker, Waldorf, MD (US); Connie H. Li, Alexandria, VA (US); Kathleen M. McCreary, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/819,987

(22) Filed: Nov. 21, 2017

(65) Prior Publication Data
US 2018/0158955 A1 Jun. 7, 2018

Related U.S. Application Data

(60) Provisional application No. 62/424,711, filed on Nov. 21, 2016, provisional application No. 62/424,722, (Continued)

(51) Int. Cl.
*H01L 29/78* (2006.01)
*G11C 11/22* (2006.01)
(Continued)

(52) U.S. Cl.
CPC ........ *H01L 29/78391* (2014.09); *G01R 33/09* (2013.01); *G11C 11/02* (2013.01);
(Continued)

(58) Field of Classification Search
CPC ............. H01L 29/78391; H01L 29/685; H01L 29/6684; H01L 29/516; H01L 27/1159;
(Continued)

(56) References Cited

U.S. PATENT DOCUMENTS 10,163,932 B1 * 12/2018 Sinitskii .............. H01L 27/1159
2006/0182004 A1 * 8/2006 Maeda ................... B82Y 10/00
369/126

(Continued)

*Primary Examiner* — David Lam
(74) *Attorney, Agent, or Firm* — US Naval Research Laboratory; Roy Roberts

(57) ABSTRACT

The invention relates to heterostructures including a layer of a two-dimensional material placed on a multiferroic layer. An ordered array of differing polarization domains and surface charges in the multiferroic layer produces corresponding domains having differing properties in the two-dimensional material. When the multiferroic layer is ferroelectric, the ferroelectric polarization domains in the layer produce local electric fields that penetrate the two-dimensional material. The local electric fields and surface charges can control the structural phase of the two-dimensional material, which in turn determines whether the two-dimensional material layer is insulating or metallic, has a band gap or no band gap, and whether it is magnetic or non-magnetic. Methods for producing the heterostructures are provided. Devices incorporating the heterostructures are also provided.

16 Claims, 4 Drawing Sheets

Related U.S. Application Data filed on Nov. 21, 2016, provisional application No. 62/577,345, filed on Oct. 26, 2017.

(51) Int. Cl.
| | |
|---|---|
| *H01L 29/66* | (2006.01) |
| *H01L 29/68* | (2006.01) |
| *G11C 11/56* | (2006.01) |
| *G11C 11/02* | (2006.01) |
| *H01L 29/51* | (2006.01) |
| *G11C 11/14* | (2006.01) |
| *G11C 13/00* | (2006.01) |
| *H01L 29/70* | (2006.01) |
| *H01L 43/08* | (2006.01) |
| *H01L 31/032* | (2006.01) |
| *G01R 33/09* | (2006.01) |
| *H01L 29/735* | (2006.01) |
| *H01L 29/739* | (2006.01) |
| *H01L 43/10* | (2006.01) |
| *H01F 10/193* | (2006.01) |
| *H01L 29/861* | (2006.01) |
| *H01L 29/24* | (2006.01) |

(52) U.S. Cl.
CPC .......... *G11C 11/14* (2013.01); *G11C 11/223* (2013.01); *G11C 11/5678* (2013.01); *G11C 13/0009* (2013.01); *H01F 10/1933* (2013.01); *H01L 29/24* (2013.01); *H01L 29/516* (2013.01); *H01L 29/6684* (2013.01); *H01L 29/685* (2013.01); *H01L 29/70* (2013.01); *H01L 29/735* (2013.01); *H01L 29/7391* (2013.01); *H01L 29/861* (2013.01); *H01L 31/0322* (2013.01); *H01L 43/08* (2013.01); *H01L 43/10* (2013.01)

(58) Field of Classification Search
CPC ... H01L 27/1158; G11C 11/02; G11C 11/223; G11C 11/5678
See application file for complete search history.

(56) References Cited

U.S. PATENT DOCUMENTS

| | | | |
|---|---|---|---|
| 2007/0072010 A1* | 3/2007 | Duan | H01L 28/55 428/701 |
| 2009/0021975 A1* | 1/2009 | Rao | G11B 9/02 365/145 |
| 2012/0281451 A1* | 11/2012 | Jiang | G11C 11/22 365/145 |
| 2016/0056003 A1* | 2/2016 | Duerig | H01L 41/09 200/181 |
| 2017/0040331 A1* | 2/2017 | Van Houdt | H01L 29/78391 |
| 2017/0099055 A1* | 4/2017 | Maksymovych | H03L 5/00 |
| 2017/0110538 A1* | 4/2017 | Nirmalraj | H01L 29/24 |
| 2017/0256552 A1* | 9/2017 | Schroder | H01L 29/78391 |

* cited by examiner

CONTROLLING STRUCTURAL PHASE TRANSITIONS AND PROPERTIES OF TWO-DIMENSIONAL MATERIALS BY INTEGRATING WITH MULTIFERROIC LAYERS

CROSS-REFERENCE TO RELATED APPLICATIONS

This application claims priority to U.S. Provisional Application No. 62/424,711, filed on Nov. 21, 2016, U.S. Provisional Application No. 62/424,722, filed on Nov. 21, 2016, and U.S. Provisional Application No. 62/577,345, filed on Oct. 26, 2017, the contents of which are incorporated herein by reference in their entirety.

TECHNICAL FIELD

This application relates generally to heterostructures including a layer of a two-dimensional material placed on a multiferroic layer. An ordered array of differing polarization domains and surface charges in the multiferroic layer produces corresponding domains having differing properties in the two-dimensional material. When the multiferroic layer is ferroelectric, the ferroelectric polarization domains in the layer produce local electric fields that penetrate the two-dimensional material. The local electric fields and surface charges can control the structural phase of the two-dimensional material, which in turn determines whether the two-dimensional material layer is insulating or metallic, has a band gap or no band gap, and whether it is magnetic or non-magnetic. Methods for producing the heterostructures are provided. Devices incorporating the heterostructures are also provided.

BACKGROUND

The conventional method for introducing an electric field and varying the carrier density in a semiconductor channel is to use an electrostatic gate consisting of a gate dielectric layer and a metal contact layer over the semiconductor transport channel. Such gates are fabricated using standard lithographic techniques, and they are normally used to apply an electric field, but their geometry is fixed once they are fabricated. The intent is to control charge flow, not determine the luminescent or chemical sensing properties. Strain is normally introduced by mechanical means.

Ferroelectric films have recently been used as the gate dielectric in transistor structures because their polarization is non-volatile (it remains after the gate voltage has been removed). A ferroelectric transistor utilizes the nonvolatile, switchable polarization field of a ferroelectric gate to control the charge carrier density in the conducting channel. This approach is actively researched as an avenue to nonvolatile transistor memory, known as ferroelectric random access memory (FeRAM).

However, the conventional methods suffer from several drawbacks. The lateral size of such a gate is determined by the limits of the lithography used to produce it, and it cannot be changed once it is fabricated. In contrast, the ferroelectric polarization is non-volatile, and the position and lateral size of the ferroelectric domains can be changed after they have been fabricated.

SUMMARY OF THE INVENTION

The invention described herein, including the various aspects and/or embodiments thereof, meets the unmet needs of the art, as well as others, by providing heterostructures including a layer of a two-dimensional material placed on a multiferroic layer. An ordered array of differing polarization domains and surface charges in the multiferroic layer produces corresponding domains having differing properties in the two-dimensional material. When the multiferroic layer is ferroelectric, the ferroelectric polarization domains in the layer produce local electric fields that penetrate the two-dimensional material. The local electric fields and surface charges can control the structural phase of the two-dimensional material, which in turn determines whether the two-dimensional material layer is insulating or metallic, has a band gap or no band gap, and whether it is magnetic or non-magnetic. Methods for producing the heterostructures are provided. Devices incorporating the heterostructures are also provided.

In accordance with one aspect of the invention, a heterostructure includes a multiferroic material layer; and a two-dimensional material layer provided on the multiferroic material layer. The multiferroic material layer comprises an array of polarization domains in the multiferroic layer, and produces corresponding domains having different structural phases in the two-dimensional material.

According to another aspect of the invention, a memory device includes a ferroelectric material layer; and a transition metal dichalcogenide (TMD) two-dimensional material layer provided on the ferroelectric material layer. The ferroelectric material layer includes an array of dipole domains in the ferroelectric material layer, and produces corresponding magnetic and non-magnetic domains in the TMD two-dimensional material.

According to a further aspect of the invention, a method for forming a heterostructure includes providing a multiferroic material layer; applying a local electric field to the multiferroic material layer, forming an array of polarization domains in the multiferroic layer; and providing a two-dimensional material layer on the multiferroic material layer having an array of polarization domains therein, wherein the polarization domains control metal-insulator phase transitions in corresponding domains in the two-dimensional material.

Other features and advantages of the present invention will become apparent to those skilled in the art upon examination of the following or upon learning by practice of the invention.

DETAILED DESCRIPTION OF EMBODIMENTS OF THE INVENTION

The invention described herein, including the various aspects and/or embodiments thereof, meets the unmet needs of the art, as well as others, by providing heterostructures including a layer of a two-dimensional material placed on a multiferroic layer. An ordered array of differing polarization domains and surface charges in the multiferroic layer produces corresponding domains having differing properties in the two-dimensional material. When the multiferroic layer is ferroelectric, the ferroelectric polarization domains in the layer produce local electric fields that penetrate the two-dimensional material. The local electric fields and surface charges can control the structural phase of the two-dimensional material, which in turn determines whether the two-dimensional material layer is insulating or metallic, has a band gap or no band gap, and whether it is magnetic or non-magnetic. Methods for producing the heterostructures are provided. Devices incorporating the heterostructures are also provided.

Figure 1A:
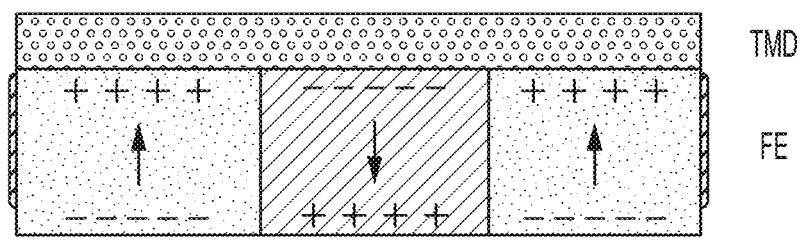
FIG. 1A is a side view of a heterostructure including a ferroelectric layer and a TMD monolayer.

The invention provides ways to control and modulate the local electric field and surface charge of one or more 2D monolayers on a nanometer length scale, by coupling the 2D materials with multiferroic materials. In particular, the structural phase transition in TMDs and therefore the corresponding properties can be controlled. In some aspects of the invention, a heterostructure is provided in which one layer is comprised of one or more 2D materials (either a single monolayer, or multiple monolayers having the same or different composition), and the adjacent layer is comprised of a multiferroic material. This multiferroic material can be a ferroelectric material, where local electrostatic domains consisting of dipole ensembles produce a local surface charge, as illustrated in FIG. 1A. If the ferroelectric material is a thin film, the strength of the electric field is related to the thickness of the film. These domains can be oriented by a global applied electric field, or manipulated at the micron to nanoscale levels with an optical beam, proximal probe such as a conducting atomic force microscope (CAFM) tip as illustrated in FIG. 4A-4E, or other techniques including optical probes.

These polarization domains in the multiferroic or ferroelectric material can directly change the properties of adjacent 2D material monolayer(s), which are strongly affected by their immediate environment due to lack of bulk screening. The dielectric screening is very low due to their two-dimensional character relative to bulk material, and the screening that would normally occur due to carriers in a three-dimensional material is largely absent. These changes in environment in turn dramatically impact the structural properties of the 2D material. Properties of 2D materials and their heterostructures can be modified and controlled by variations in the local electric field and surface charge induced by local dipoles in an adjacent ferroelectric layer. This effect and mechanism is distinct from an electric field due to a voltage applied by a standard gate terminal, or charge doping by chemical treatment or surface adsorbates.

Heterostructures and Devices.

The heterostructures of the invention include a multiferroic material layer adjacent to (and preferably directly in contact with) one or more two-dimensional material layers.

The two-dimensional ("2D") materials of the invention may be provided in the heterostructure as a single monolayer, or provided as multiple monolayers. When multiple monolayers are used, preferably from 2 to 20 monolayers are provided, more preferably from 2 to 10, still more preferably from 3 to 6. The monolayers may be formed from a variety of materials, including transition metal dichalcogenides ("TMDs"), silicene, phosphorene, and graphene. The TMDs for use in the apparatus and methods of the invention have the chemical formula $MX_2$, where M is a transition metal, and X is a chalcogen.

Transition metals include elements from Groups 3-12 of the periodic table. The transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, Hs, Mt, Ds, Rg, and Cn, as well as the lanthanide series elements (La, Ce, Pr, Nd, Pm, Sm, Eu, Gd, Tb, Dy, Ho, Er, Tm, Yb, and Lu), and actinide series elements (Ac, Th, Pa, U, Np, Pu, Am, Cm, Bk, Cf, Es, Fm, Md, No, Lr). Preferred transition metals for use in the apparatus and methods of the invention include Mo, W, Nb, Hf, Ta, and V, with Mo, W, Nb, and Ta being particularly preferred.

Chalcogens include the elements found in Group 16 of the periodic table. The chalcogens include O, S, Se, Te, and Po. Preferred chalcogens for use in the apparatus and methods of the invention include S, Se, and Te, with S and Se being particularly preferred.

In some aspects of the invention, preferred 2D TMD materials may be selected from the group consisting of $MoS_2$, $MoSe_2$, $WS_2$, $WSe_2$, $VS_2$, $VSe_2$, $VTe_2$, $NbS_2$, $NbSe_2$, $TaS_2$, $TaSe_2$, and combinations thereof. Additional TMD materials formed from the transition metals and chalcogens set forth above are also within the scope of the invention.

The multiferroic material can be any material that exhibits more than one primary ferroic order parameter (which include ferromagnetism, ferroelectricity, and ferroelasticity). In some aspects of the invention, the multiferroic material is a ferroelectric (FE) material, where local electrostatic domains consisting of dipole ensembles exist and produce a local electric field, modifying the dielectric environment. These local domains modify and control the optical, transport and other electronic properties of the two-dimensional material. The multiferroic materials may include, but are not limited to, $BiMnO_3$, $LaMnO_3$, and $BiFeO_3$, and combinations thereof. Ferroelectric materials may include, but are not limited to, lead zirconate titanate (PZT), barium titanate, lead titanate, lead magnesium niobate-lead titanate (PMN-PT), and combinations thereof. Composites of any of these materials may also be used.

The multiferroic layer used in the invention may be provided as a bulk substrate or thin film. When the multiferroic layer is a thin film, it may range from about 1 nm in thickness up to many microns in thickness. The thin film may optionally be supported by a substrate material such as silica ($SiO_2$), silicon, $SiO_2$/Si, or sapphire, but the invention is not limited to any particular substrate material. For example, growth of multiferroic or ferroelectric thin films on periodically poled wafers may be preferred in some aspects of the invention, to provide laterally templated growth of layers deposited thereon. Examples of substrates that may be provided, optionally as templated substrates, are lithium niobate and strontium titanate.

The 2D material monolayers of the invention may be exfoliated, mechanically transferred, or grown directly on the multiferroic or ferroelectric material by deposition techniques such as chemical vapor deposition. For example, multiple methods are available to mechanically transfer TMD monolayers, such as $WS_2$, onto alternate substrates, such as multiferroic or ferroelectric films. The transfers may be conducted using a thin layer of a transfer material, such as a PMMA (polymethyl methacrylate), PC (polycarbonate), or PDMS (polydimethylsiloxane)/PC film. The direct integration of the multiferroic with the 2D material results in the smallest possible separation (≤1 nm) between the two, thereby maximizing the electric field resulting from the polarization domains in the ferroelectric material. There is no intervening dielectric layer, as there is in a conventional electrostatic gate contact. Because the ferroelectric dipole electric field decreases with distance R, and corresponds to approximately $R^{-3}$, the electric field strength at the 2D layer is as large as it can be when the 2D material lies directly on top of the ferroelectric layer. This electric field penetrates the 2D material layer and modifies its properties.

Ferroelectric materials exhibit a spontaneous polarization due to internal electric dipoles which are coupled to the lattice. See M. E. Lines, et al., *Principles and Applications of Ferroelectrics and Related Materials*, Oxford University Press, Oxford, England (1977), page 525. Typical examples include $BaTiO_3$, $BiFeO_3$, and $PbTiO_3$. They can be polarized in a particular direction and manner by a global applied electric field—this polarization is retained even after the electric field is removed (this is analogous to a magnetic material which exhibits a spontaneous magnetization, and the magnetization is retained in the absence of an applied magnetic field). The polarization can also be reversed by a global applied electric field, and the hysteresis depends upon factors that are both intrinsic (e.g., coupling of the internal dipoles to the lattice) and extrinsic (e.g., interfaces, sample structure and aspect ratio).

Ensembles of these dipoles form local domains within the ferroelectric material, with a net polarization oriented in a particular direction (up or down), just as magnetic domains exist in a ferromagnet. See X. Hong, et al., "Emerging ferroelectric transistors with nanoscale channel materials: the possibilities, the limitations," *J. Phys. Condens. Matter* 28, 103003 (2016). The invention beneficially provides methods for forming local domains in the heterostructures and devices, which can be oriented and manipulated on length scales ranging from a single nanometer to several microns, by application of a highly localized electric field applied, for example, using proximal probe techniques, such as through a voltage applied between the ferroelectric material surface and the tip of an atomic force microscope (AFM), which is preferably operated as a conducting atomic force microscope (CAFM). Isolated domains can be created in predetermined locations, or an ordered array of domains may be fabricated. Thus, the properties of the adjacent 2D materials can be controlled and modified with the same spatial resolution, i.e., if a 10 µm×10 µm checkerboard pattern is created in the ferroelectric material, the properties of the 2D material layer will also be modified in a 10 µm×10 µm pattern.

The heterostructures of the invention allow for writing and rewriting the polarization domains of the ferroelectric material in any order, size, spacing, or period, and at any time, in a non-destructive and reversible fashion, permitting the heterostructures to form the basis of a reconfigurable electronic system. The polarization domains may be provided in any arrangement, without limitation. Exemplary polarization domain configurations include a checkerboard pattern, or concentric shapes (including, without limitation, squares, rectangles, circles, ovals, shapes exhibiting one or more axes of symmetry, or irregular shapes). The polarization domains are non-volatile, and no refresh power is required. The heterostructures also permit a global erase function, which may be achieved when a global electric field is used to erase any domains written in the ferroelectric layer.

When used in devices, the heterostructures of the invention may optionally be combined with any suitable components, including, but not limited to, electronic contacts, and electromagnetic signal transmitters. Signal transmitters may optionally be used, for example, to generate a signal to indicate that the 2D material layer has interacted with an agent of interest. However, it is to be appreciated that one of the benefits of the invention is the simplified fabrication that it permits by eliminating deposition and lithography steps necessary to deposit and define dielectric layers and top metal layers, as no discrete insulating dielectric layer or top metal contact are required to introduce the local electric fields. In addition, the invention offers lateral spatial resolution that is comparable to or better than that available with existing lithographic techniques.

The heterostructures of the invention may be used in a device that is capable of operating based on modifications in carrier density, transport properties, optical properties, surface chemistry, piezoelectric-induced strain, magnetic properties, and/or interlayer spacing. Such devices may include, but are not limited to, nonvolatile memory, low power electronics, reprogrammable logic gates, chemical vapor sensors, and tunable optical devices. The local electric fields can control the structural phase of the two-dimensional material, which in turn determines whether the two-dimensional material layer is insulating or metallic, has a band gap or no band gap, and whether it is magnetic or non-magnetic. The ability to use an electric field to switch the MIT or control magnetic order has broad application in nonvolatile memory, information processing, and electronics with low- and ultra-low-power consumption.

Structural Phase Transitions in 2D Materials.

Single monolayer TMDs exhibit two structural phases, designated honeycomb (H) and centered honeycomb (T). These phases are designated as 2H and 1T in the literature when there are two or more layers present. An intermediate phase that is a distorted version of the T phase is designated T' (1T' when two or more layers are present). The H phase is typically insulating or semiconducting, and the T and T' phases are typically metallic. The H(2H) phase is typically the thermodynamically stable phase for many TMD materials, while the T(1T) and T'(1T') phases have slightly higher energies and are metastable. TMDs having a smaller energy difference between the H and T,T' phases are ideal candidates for use in the heterostructures of the invention, such as $MoTe_2$ and $WTe_2$. See K. A. N. Duerloo, et al., "Structural phase transitions in two-dimensional Mo- and W-dichalcogenide monolayers," *Nat. Commun.* 5, 4214 (2014). However, even TMDs with a relatively large energy difference between the H and T,T' phases can be reversibly switched between these phases by adding or subtracting charge. For example, $MoS_2$ can be switched from the H phase to the T,T' phase by adding electrons by immersing the surface in n-butyl lithium, and then converted back to the H phase by annealing the sample to drive off the electron-donating adsorbates. See R. Kappera, et al., "Phase-engineered low resistance contacts for ultrathin $MoS_2$ transistors," *Nat. Mater.* 13, 1128 (2014).

Polarization domains in the multiferroic material layers of the invention are non-volatile (i.e., they remain when the voltage or electric field is removed) and accompanied by either positive or negative surface charge accumulation depending upon the orientation of the polarization dipole. This surface charge density may be at least as high as about $5 \times 10^{12}$ cm$^{-2}$, and may preferably be at least about $5 \times 10^{14}$ cm$^{-2}$, which is orders of magnitude higher than can be achieved in a conventional two dimensional electron gas (2DEG). It is comparable to the surface atom density of a TMD material such as MoTe$_2$, and thus offers one unit charge (electron or hole) for every surface atom of the TMD monolayer. This localized surface charge can change the carrier density in an adjacent layer of a 2D material, such as a TMD, and thereby control the structural phase in a reversible, non-volatile manner on the few nm length scale. This procedure is completely different from immersing the TMD in a solution of n-butyl lithium to add electrons, and then annealing it to desorb the electron-donating adsorbate molecules.

The structural phase (H, T, or T') determines many properties of the TMD monolayer, e.g. whether the monolayer is insulating or metallic, has a band gap (with optical emission properties) or no band gap, or is magnetic or non-magnetic. The H phase can be converted to the T or T' phase by electron doping accomplished by immersing the H surface in liquid n-butyl lithium. The T and T' phases are metastable, and convert back to the H phase when the electron doping is removed by annealing. The invention provides a method and heterostructure for controlling that electron doping by the surface charge of the polarization domains in an adjacent ferroelectric layer.

Figure 1B:
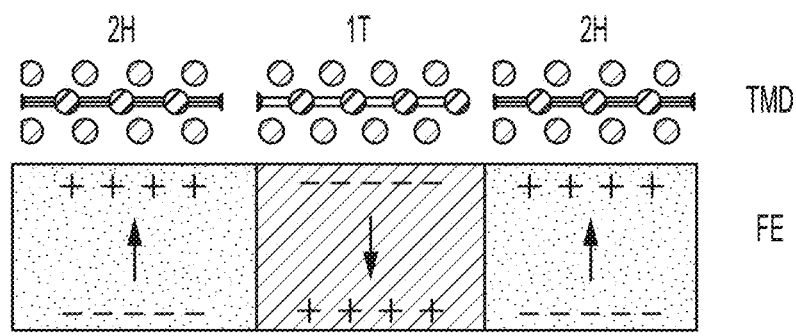
FIG. 1B is a side view depicting the structural changes in the TMD monolayer resulting from variations in the local electric field and surface charge of the ferroelectric layer.

As shown in FIG. 1B from left to right, when the TMD lies over a region of the ferroelectric layer where the polarization dipole points along the surface normal out of the plane of the film (arrow pointing up), the positive surface charge on the ferroelectric surface offers no free electrons, and therefore the H phase of the TMD remains stable. When the polarization dipole in the ferroelectric layer points into the film (arrow pointing down), a negative surface charge layer is created which dopes the adjacent TMD layer with excess electrons, converting it from the stable H phase (insulating) to the metastable metallic T or T' phase. When the polarization dipole in the FE layer is switched to point out of the film along the surface normal, a positive surface charge layer is again created which dopes the adjacent TMD layer with excess holes, converting it from the metastable metallic T or T' phase back to the stable insulating H phase. Thus by reversing the orientation of the polarization dipole in the ferroelectric layer, the structural phase can be controlled, and accordingly whether the TMD is metallic or insulating. The nonvolatile character of the ferroelectric dipole polarization means that the TMD will remain metallic or insulating until the ferroelectric dipole is reversed. This provides control over the metal-to-insulator transition (MIT) in the TMD layer.

The invention uses the charge doping provided by the ferroelectric polarization domains to control the structural phase and corresponding magnetic character of an adjacent TMD layer. For example, changing the electron density in select TMD materials such as $VX_2$ (where X=S, Se, or Te) results in reversible stabilization of either the H or T phase, and thereby changes the material from a high-spin to low-spin magnetic system, or converts it from a non-magnetic material to a ferromagnetic material. In VTe$_2$, the T phase is predicted to be non-magnetic, while the H phase is predicted to be ferromagnetic. See C. Ataca, et al., "Single layer MX$_2$ transition metal oxides and dichalcogenides in a honeycomb-like structure," *J. Phys. Chem* C116, 8983-8999 (2012).

The surface charge of the ferroelectric domains (as illustrated in FIG. 1A) alters the photoluminescence (PL) of an adjacent TMD layer, for example, WS$_2$. The PL is more intense from areas of the WS$_2$ over a polarization domain with positive surface charge, and much less intense from areas of the WS$_2$ or a polarization domain with a negative surface charge, as shown in FIGS. 4D and 4E. This was interpreted in terms of charge doping of the WS$_2$ from the ferroelectric layer.

In accordance with another aspect of the invention, the dipoles in the ferroelectric material layer modify the structural phase of the 2D monolayer(s). The structural phase strongly affects corresponding properties (metal-insulator transition, magnetic—nonmagnetic transition) of single or few monolayer materials such as the transition metal dichalcogenides (TMDs), and is controlled by the charge doping or electric fields produced by the polarization dipole domains in an adjacent ferroelectric (FE) layer. An ordered array of polarization domains of the ferroelectric material produces a corresponding ordered variation in structural phase of the 2D material. For example, arrays of magnetic domains may be advantageous when the heterostructures of the invention are used in a memory device. The configuration of the magnetic domains, whether magnetic or non-magnetic, may be used to reversibly encode 1 and 0 bits.

Methods.

The invention also provides methods for forming heterostructures, including, but not limited to, the heterostructures described herein. The methods include providing a multiferroic material layer and applying a local electric field to the multiferroic material layer in order to create one or more polarization domains in the multiferroic layer. For example, when the multiferroic material layer is a ferroelectric material layer, the polarization domains may comprise dipole domains.

The local electric field may be applied, for example, using an optical beam, a proximal probe (such as a conducting atomic force microscope tip), or other techniques including optical probes. When a conducting atomic force microscope is used, it may be operated at a bias voltage of from ±1 V to ±10 V. When the multiferroic material layer is a ferroelectric material, a positive tip voltage will result in polarization dipoles in the ferroelectric layer that point into the sample plane, and a negative charge at the surface of the ferroelectric layer. A negative tip voltage will result in polarization dipoles in the ferroelectric layer that point out of the sample plane, and a positive charge at the surface of the ferroelectric layer. An image of the poled surface may also be obtained using the atomic force microscope by operating it in EFM phase mode.

The polarization domains may be provided in any size, shape, pattern, or configuration that is desired, based on the properties or functions of the specific heterostructure being formed. The polarization domains may range from a nanometer scale (i.e., features having a width on the order of 1 nm or more) to multiple micron scale (i.e., features having a width on the order of 1 micron, 5 microns, 10 microns, or more). Polarization domains may be separated by domain walls having any desired width. In some aspects of the invention, the polarization domain wall width may be as low as from 1-10 nm, though wider domain walls are also included in the scope of the invention.

In some aspects of the invention, the local electric fields may be globally erased, for example, by exposing the entire multiferroic material layer, or the entire heterostructure, to a global electric field. Once erased, the multiferroic material layer may have new local electric fields applied. The process of globally erasing the polarization domains and providing a new configuration of polarization domains may be repeated multiple times. In other aspects of the invention, the polarization domains may be modified only in desired locations, by applying appropriate local electric fields to areas having polarization domains to be changed.

The local electric field may be applied to the multiferroic material layer prior to depositing a 2D material layer thereon, or it may be applied after the heterostructure including the multiferroic layer and 2D material layer has been formed. Regardless of the order of these steps, the polarization domains in the multiferroic material layer produce corresponding domains in the two-dimensional material layer that is provided on the multiferroic material layer. The term "corresponding domains" is used to refer to domains in a 2D material layer that is part of a heterostructure, where the domains have properties (such as those described above) that are influenced by or result from proximity to a polarization domain of a multiferroic material. These domains are typically positioned opposite to a polarization domain formed in a multiferroic material.

The 2D material layer may be applied to the multiferroic material layer using a technique selected from the group consisting of mechanical exfoliation, mechanical transfer, and growth directly on the multiferroic material layer.

The 2D material layer may be applied directly to a multiferroic material layer in some aspects of the invention. When the 2D material layer is applied to a substrate and is transferred to the multiferroic layer, the transfer may be carried out using mechanical techniques. Regardless of the material to which it is applied, the 2D material layer may be deposited by chemical vapor deposition or other deposition or growth technique to a thickness of 1 monolayer (which is about 0.7 nm thick for a TMD monolayer, but those skilled in the art will appreciate that the thickness of the monolayer will depend on the specific monolayer composition). More than one monolayer may also be applied to form the 2D material layer, either by sequential application of layers or by depositing multiple layers simultaneously.

EXAMPLES

Aspects of the invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1

Figure 2A:
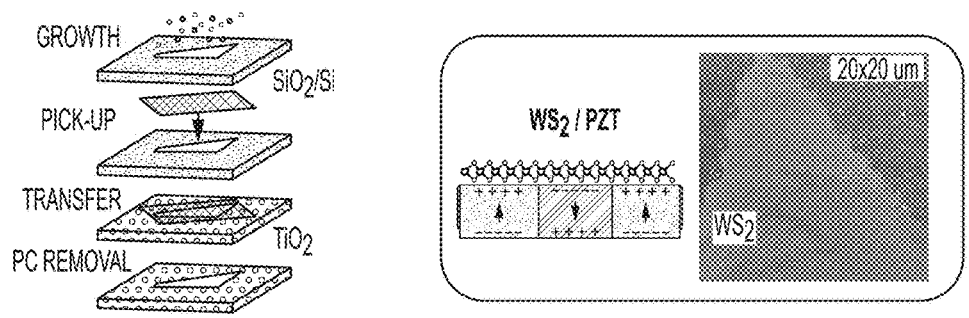
FIG. 2A depicts steps involved in a two-dimensional ("2D") material transfer process, along with a depiction of a structure formed by the process, and an image of a $WS_2$ monolayer transferred using the process.
Figure 2B:
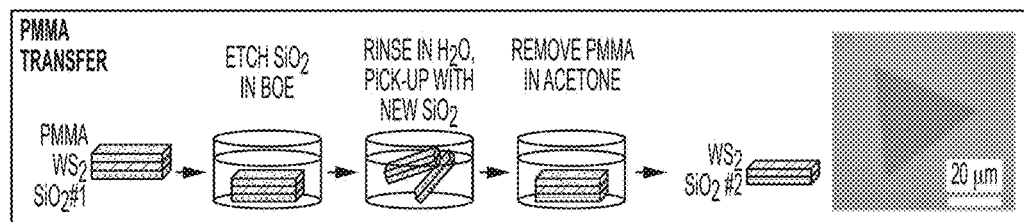
FIG. 2B depicts a PMMA film transfer method.

One method for mechanically transferring a TMD monolayer, such as $WS_2$, onto a substrate, such as a ferroelectric film, includes the use of a PMMA film, as illustrated in FIG. 2B. A sample including a layer of $WS_2$ on an $SiO_2$ substrate is coated with a thin layer of PMMA (polymethyl methacrylate) resist and cured on a hot plate at 100° C. for 10 minutes, then submerged in buffered hydrofluoric acid to etch the $SiO_2$, freeing the $WS_2$ from the growth substrate. Once fully etched, the film was rinsed in deionized $H_2O$, where it floated on the surface, and was then lifted from the water using the desired substrate. Optionally, adhesion of the $WS_2$ layer may be improved by spinning at 2000 rpm and baking at 100° C. An acetone and isopropanol soak removes the PMMA. An optical image of PMMA transferred $WS_2$ exhibits a uniform, clean, triangular shape, and is also shown in FIG. 2B.

Example 2

Figure 2C:
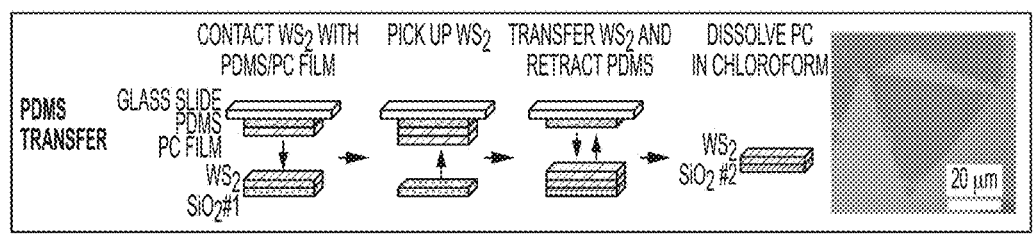
FIG. 2C depicts a PDMS film transfer method.

Another method for mechanically transferring a TMD monolayer, such as $WS_2$, onto a substrate, such as a ferroelectric film, includes the use of a PDMS/PC film, as illustrated in FIG. 2C. A sample including a layer of $WS_2$ on an $SiO_2$ substrate is brought into contact a PDMS/PC film, then retracted. This moves the $WS_2$ from $Si/SiO_2$ onto the PDMS/PC film. The PDMS/PC/$WS_2$ stack is then placed onto clean $Si/SiO_2$. The PDMS stamp is retracted, leaving the PC film on the top surface of $WS_2$, which is then dissolved in chloroform. An optical image following PDMS transfer is shown in FIG. 2C.

Example 3

Polarization domains were written into a 150 nm PZT/Pt/$SiO_2$/Si test sample using a conductive atomic force microscope (CAFM) manufactured by Park Systems (Suwon, South Korea), in order to demonstrate that polarization domains in the ferroelectric film control photoluminescence (PL) intensity of mechanically transferred $WS_2$ monolayers. The sample is shown in FIG. 3

Figure 3:
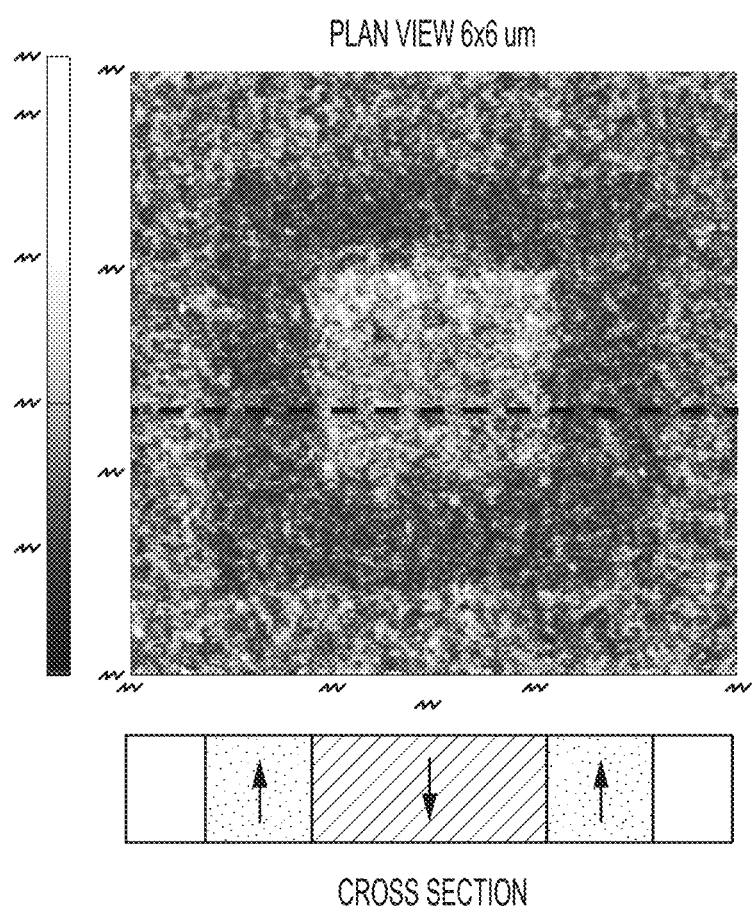
FIG. 3 depicts an exemplary configuration for polarization domains, written into a 150 nm $PZT/Pt/SiO_2/Si$ test sample using a conductive atomic force microscope (CAFM).

The 6×6 micron image shown in FIG. 3 was obtained using the AFM operating in electric force microscopy imaging mode. The dark regions of the image correspond to the areas of the sample in which the AFM created dipole domains pointing up. The light regions of the image correspond to the areas of the sample in which the AFM created dipole domains pointing down. This is shown schematically in the accompanying cross section corresponding to the fiducial line drawn through the image. While the dipole domains shown here are about 500 nm in lateral dimension, domains on the scale of a few nanometers can also be successfully created and imaged.

Example 4

A large area monolayer $WS_2$ grown by a CVD process on a $SiO_2$/Si substrate in a 2 inch tube furnace. $WO_3$ powder and sulfur precursors were heated to 825° C. under a 100 sccm argon and 10 sccm hydrogen flow. Perylene-3,4,9,10-tetracarboxylic acid tetrapotassium salt was used as seed molecules to promote lateral growth. The monolayer nature was confirmed by Raman and PL mapping.

The $WS_2$ film was removed from the $SiO_2$/Si growth substrate and transferred onto a 100 nm thick PZT film on a conducting n-type strontium titanate wafer. Transfer was conducted using the method of Example 1. Before transfer, a metal marker grid pattern (Ti/Au) was deposited on the PZT film using either a shadow mask or photolithography technique, in order to assist in locating specific poled areas.

Polarization domains were written into the PZT film using a C-AFM (Park Systems NX-10), which was operated using dc voltages of up to ±10 V, using two types of cantilevers: Cr—Pt coated (Multi75E, Budget Sensors) and Au-coated (PPP-NCSTAu, Nanosensors) Si cantilevers. Similar results were obtained with both. A tip voltage of ±10 V direct current (dc) was applied in the contact mode, and polarization domains were written in a checkerboard pattern. Line scan densities of at least 512 lines per 10 μm were used to write the polarization domains into the PZT in a checkerboard pattern with the tip polarities shown. Dynamic contact electrostatic force microscopy was used to image the polarization state of the poled regions, at a frequency of 75-160 kHz. The total image size is 30×30 μm, and each poled square is 10×10 μm. The dashed lines are provided as a guide, and the bias voltages applied to the C-AFM tip are indicated.

Figure 4A:
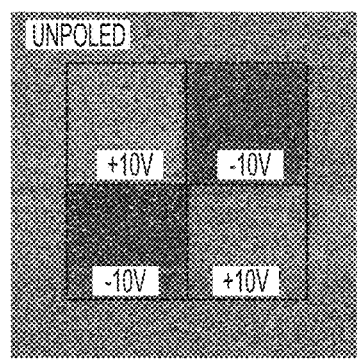
FIG. 4A is an image of a 100 nm PZT film surface poled using an atomic force microscopy (AFM) operated in the electrostatic force microscopy phase mode.

An image of the poled 100 nm PZT surface was obtained using the same AFM operated in the electrostatic force microscopy phase mode, and an EFM phase image of the area is shown in FIG. 4A.

Figure 4B:
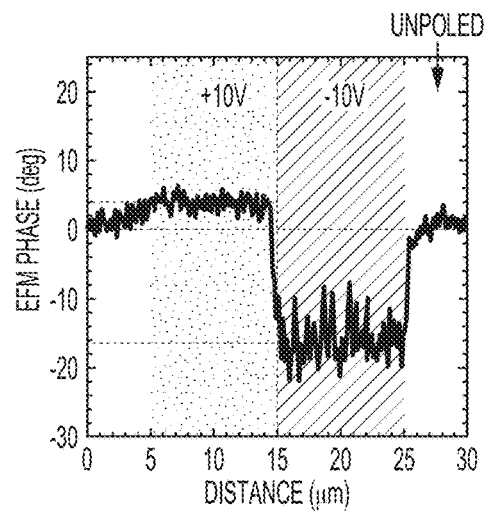
FIG. 4B is a horizontal EFM line scan averaged left to right across the top two panels of the checkerboard of FIG. 4A.
Figure 4C:
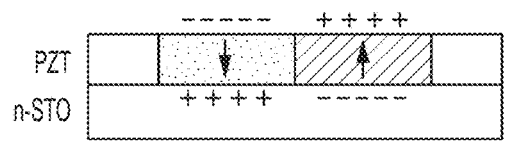
FIG. 4C is a schematic cross section of the PZT film, illustrating the orientation of the polarization domains and the corresponding surface charge.
Figure 4D:
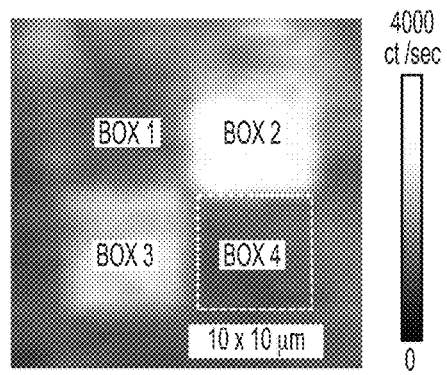
FIG. 4D is a PL peak intensity map obtained from the $WS_2$ monolayer.
Figure 4E:
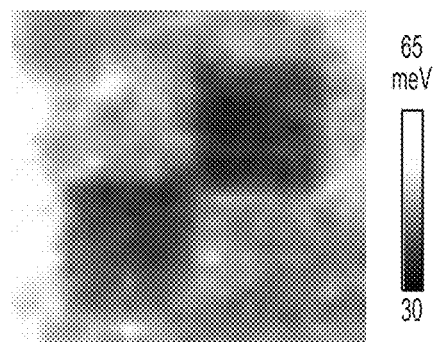
FIG. 4E is a spatial map of the PL linewidth (FWHM) corresponding to the data of FIG. 4D.

FIG. 4B shows a horizontal EFM line scan averaged left to right across the top two panels of the checkerboard pattern. There is strong contrast between the squares written with opposite AFM tip polarities, indicating successful poling of the PZT film. There is little contrast between the areas of PZT that were not poled by the AFM and the squares that were intentionally poled using a +10 V tip bias, due to global poling of the entire PZT film before application of the AFM. FIG. 4C shows a schematic cross section of the PZT film illustrating the orientation of the polarization domains and corresponding surface charge.

A PL peak intensity map was obtained from the $WS_2$ monolayer over a 30×30 μm area in the sample plane, acquired from a region of the PZT that was intentionally poled by the AFM with the checkerboard pattern, as shown in FIG. 4D. A spatial map of the PL linewidth (FWHM) corresponding to the data of FIG. 4D is shown in FIG. 4E.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A heterostructure comprising:
   a multiferroic material layer; and
   a two-dimensional material layer provided directly on the multiferroic material layer,
   wherein the multiferroic material layer comprises an array of polarization domains having different surface charges, and the different surface charges produce corresponding domains having different structural phases in the two-dimensional material,
   wherein the polarization domains in the multiferroic ferroelectric material layer produce local electric fields and surface charges that penetrate the two-dimensional material layer, and
   wherein the local electric fields and surface charges create local magnetic and non-magnetic domains in the two-dimensional material layer.

2. The heterostructure of claim 1, wherein the multiferroic material layer is a ferroelectric material layer.

3. The heterostructure of claim 2, wherein the ferroelectric material layer is selected from the group consisting of lead zirconate titanate (PZT), barium titanate, lead titanate, lead magnesium niobate-lead titanate (PMN-PT), and combinations thereof.

4. The heterostructure of claim 1, wherein the multiferroic material layer is selected from the group consisting of $BiMnO_3$, $LaMnO_3$, and $BiFeO_3$, and combinations thereof.

5. The heterostructure of claim 1, wherein the two-dimensional material layer is selected from the group consisting of transition metal dichalcogenide (TMD), silicene, phosphorene, graphene, and combinations thereof.

6. The heterostructure of claim 5, wherein the two-dimensional material layer is a TMD selected from the group consisting of $MoS_2$, $MoSe_2$, $WS_2$, and $WSe_2$.

7. A device comprising the heterostructure of claim 1.

8. The device of claim 7, wherein the device is selected from the group consisting of non-volatile memory, low power electronics, reprogrammable logic, chemical vapor sensors, and tunable optical devices.

9. A memory device, comprising:
   a ferroelectric material layer; and
   an transition metal dichalcogenide (TMD) two-dimensional material layer provided directly on the ferroelectric material layer,
   wherein the ferroelectric material layer comprises an array of dipole domains having different surface charges, and the different surface charges produce corresponding magnetic and non-magnetic domains in the TMD two-dimensional material,
   wherein the polarization domains in the ferroelectric material layer produce local electric fields and surface charges that penetrate the TMD two-dimensional material, and
   wherein the local electric fields and surface charges create local magnetic and non-magnetic domains in the TMD two-dimensional material.

10. The memory device of claim 9, wherein the magnetic domains in the TMD two-dimensional material reversibly encode 1 and 0 bits.

11. A method for forming a heterostructure, comprising:
    providing a multiferroic material layer;
    applying a local electric field to the multiferroic material layer, forming an array of polarization domains in the multiferroic layer having different surface charges;
    providing a two-dimensional material layer directly on the multiferroic material layer having an array of polarization domains therein, wherein the different surface charges in the polarization domains produce metal-insulator phase transitions in corresponding domains in the two-dimensional material,
    wherein the polarization domains in the multiferroic ferroelectric material layer produce local electric fields and surface charges that penetrate the two-dimensional material layer, and
    wherein the local electric fields and surface charges create local magnetic and non-magnetic domains in the two-dimensional material layer.

12. The method of claim 11, wherein the local electric field is applied by an atomic force microscope.

13. The method of claim 11, wherein the two-dimensional material layer is provided using a technique selected from the group consisting of mechanical exfoliation, mechanical transfer, and growth directly on the multiferroic material layer.

14. The method of claim 11, further comprising applying a global electric field to erase the polarization domains in the multiferroic layer.

15. The method of claim 14, further comprising applying a local electric field to form a second array of polarization domains in the multiferroic layer.

16. The method of claim 11, wherein the multiferroic material layer is a ferroelectric material layer, and the polarization domains comprise dipole domains.

* * * * *